United States Patent [19]

Sunley et al.

[11] 4,116,674
[45] Sep. 26, 1978

[54] PROCESS OF SEVERELY DAMAGING OR KILLING UNWANTED PLANTS WITH PYRIMIDINE COMPOUNDS

[75] Inventors: Raymond Leo Sunley; Geoffrey David Snowling, both of Woodley, England

[73] Assignee: Imperial Chemical Industries Limited, London, England

[21] Appl. No.: 597,572

[22] Filed: Jul. 21, 1975

[30] Foreign Application Priority Data

Aug. 5, 1974 [GB] United Kingdom ............... 34335/74

[51] Int. Cl.$^2$ .............................................. A01N 9/22
[52] U.S. Cl. ........................................ 71/92; 542/400; 542/429; 542/458; 542/468; 544/122; 544/253; 544/320; 544/321; 544/323; 544/325; 544/330
[58] Field of Search ..................... 71/92; 260/256.4 C, 260/256.4 N, 247.5 D

[56] References Cited

U.S. PATENT DOCUMENTS

| | | | |
|---|---|---|---|
| 2,610,187 | 9/1952 | Oroshnik | 260/256.4 C |
| 2,691,655 | 10/1954 | Hitchings et al. | 260/256.4 N |
| 2,710,867 | 6/1955 | Rorig et al. | 260/256.4 C |
| 2,755,298 | 7/1956 | Whittaker | 260/256.4 N X |
| 2,983,727 | 5/1961 | Lyttle et al. | 260/256.4 N |
| 3,284,188 | 11/1966 | Amagasa et al. | 71/92 X |
| 3,287,453 | 11/1966 | McHattie | 260/256.4 C |
| 3,624,084 | 11/1971 | Mathieu | 260/247.5 D X |
| 3,705,159 | 12/1972 | Schneider et al. | 71/92 X |
| 3,845,055 | 10/1974 | Hoegerle et al. | 71/92 X |

FOREIGN PATENT DOCUMENTS

| | | | |
|---|---|---|---|
| 7,011,564 | 2/1971 | Netherlands | 71/92 |
| 1,182,584 | 2/1970 | United Kingdom. | |
| 822,069 | 10/1959 | United Kingdom. | |

OTHER PUBLICATIONS

C.A., 82 (1975), 107423k, ECK et al.
C.A., 55 (1961), 2005d, Geigy.

*Primary Examiner*—Joseph Paul Brust
*Attorney, Agent, or Firm*—Cushman, Darby & Cushman

[57] ABSTRACT

A process of severely damaging or killing unwanted plants, which comprises applying to the plants, or to the growth medium thereof, a herbicidally effective amount of pyrimidine compound of the formula:

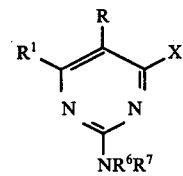

or a herbicidal acid addition salt thereof, wherein $R^1$ is an alkyl radical of 1 to 6 carbon atoms, cycloalkyl or alkenyl; R is a hydrogen atom or an alkyl or alkenyl radical of from 1 to 12 carbon atoms, which may be substituted by a phenyl radical; or $R^1$ and R taken together form a trimethylene or tetramethylene radical; X is either (a) an —$NR^3R^4$ radical wherein each of the groups $R^3$ and $R^4$ is a hydrogen atom or an alkyl or alkenyl radical of 1 to 3 carbon atoms or cycloalkyl, or —$NR^3R^4$ constitutes a pyrrolidinyl, piperidinyl or morpholinyl ring; or (b) a group —$OR^5$ wherein $R^5$ is an alkyl or alkenyl radical of 1 to 10 carbon atoms or cycloalkyl; and $R^6$ and $R^7$ each represent hydrogen or an alkyl or alkenyl radical of 1 to 8 carbon atoms, or cycloalkyl, or $R^6$ and $R^7$, taken together with the nitrogen atom to which they are attached constitute a pyrrolidinyl, piperidinyl, or morpholinyl ring; provided that R may be hydrogen only when X is an $OR^5$ group.

6 Claims, No Drawings

PROCESS OF SEVERELY DAMAGING OR KILLING UNWANTED PLANTS WITH PYRIMIDINE COMPOUNDS

This invention relates to herbicidal pyrimidine compounds and to herbicidal processes and compositions utilising such compounds.

According to the present invention, there is provided a process of severely damaging or killing unwanted plants, which comprises applying to the plants, or to the growth medium thereof, a pyrimidine compound of the formula:

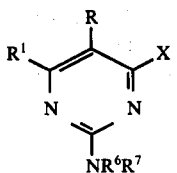

or an acid addition salt thereof, wherein $R^1$ is an aliphatic or alicyclic group; R is a hydrogen atom or an aliphatic or alicyclic group optionally substituted by phenyl or R and $R^1$ together form a trimethylene or tetramethylene radical; X is either (a) an —$NR^3R^4$ group wherein each of the groups $R^3$ and $R^4$ is a hydrogen atom or an aliphatic or alicyclic group, or wherein $R^3$ and $R^4$, taken with the nitrogen atom to which they are attached, form a 5- or 6-membered heterocyclic ring, or (b) a group —$OR^5$ where $R^5$ is an aliphatic or alicyclic group; and $R^6$ and $R^7$ each represent a hydrogen atom or an aliphatic or alicyclic group, or $R^6$ and $R^7$, taken together with the nitrogen atom to which they are attached, form a 5- or 6-membered heterocyclic ring; provided that R may be hydrogen only when X is an $OR^5$ group. By the term "aliphatic and alicyclic groups" in the foregoing discussion we mean such groups containing up to, but not more than 18 carbon atoms, and this definition applies throughout the rest of this specification and claims.

Examples of values for the group $R^1$ include, for example, alkyl cycloalkyl, and alkenyl radicals. $R^1$ may be, for example, an alkyl group of from 1 to 6 carbon atoms, for example a methyl group. Examples of values for the group R include, for example, alkyl and alkenyl radicals. R may be, for example, an alkyl or alkenyl radical of 1 to 12 carbon atoms, more particularly from 1 to 8 carbon atoms, optionally substituted by a phenyl radical.

When the group X is an —$NR^3R^4$ group, each of the groups $R^3$ and $R^4$ may be, for example, a hydrogen atom or a lower alkyl or alkenyl radical, for example an alkyl or alkenyl radical of 1 to 3 carbon atoms. When $R^3$ and $R^4$, together with the nitrogen atom to which they are attached, form a 5- or 6-membered heterocyclic ring, the heterocyclic ring may be, for example, pyrrolidine, piperidine, or morpholine.

When the group X is an —$OR^5$ radical, the group $R^5$ may be, for example, an alkyl (including cycloalkyl) or alkenyl radical. Examples of such alkyl and alkenyl radicals include those having from one to ten carbon atoms.

With reference to the group —$NR^6R^7$, each of the groups $R^6$ and $R^7$ may be, for example, a hydrogen atom or an alkyl cycloalkyl or alkenyl radical. More particularly, each of the groups $R^6$ and $R^7$ may be for example an alkyl or alkenyl radical of from 1 to 8 carbon atoms.

Within this range, each group $R^6$ and $R^7$ may be for example an alkyl or alkenyl group of 1 to 6 carbon atoms. When the group —$NR^6R^7$ constitutes a 5- or 6-membered heterocyclic ring, it may for example be a pyrrolidine, piperidine, or morpholine ring.

The identity of the acid which is used to form the acid addition salts of compounds used in the process of the invention is not critical and a wide variety of acid addition salts of any particular compound may therefore be used. For reasons of convenience and economy, however, salts derived from the readily available mineral acids are preferred, although others may be used if desired. In considering the choice of acid, the purpose for which the salt is to be used will be taken into account; salts formed from herbicidal acids which are highly persistent in the soil would obviously not be suitable for applications in which crops are to be planted shortly after the herbicide is applied. Particular examples of acids which may be used to form the acid addition salts include hydrochloric, hydrobromic, sulphuric, nitric, and phosphoric acids.

Within the class of compounds defined above for use in the process of the invention, several sub-classes may be distinguished. One such sub-class, for example, comprises compounds of the formula (I) below:

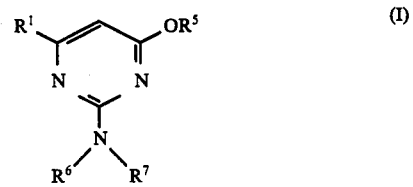

and acid addition salts thereof, wherein $R^1$, $R^5$ and —$NR^6R^7$ have any of the values previously assigned to them. Preferably, $R^1$ is an alkyl group of 1 to 4 carbon atoms, for example a methyl group. In the group —$NR^6R^7$, one of the groups $R^6$ and $R^7$ is preferably a hydrogen atom and the remaining group is preferably an alkyl or alkenyl radical of from 1 to 8 carbon atoms. The group $R^5$ is preferably an alkyl radical of from 3 to 4 carbon atoms.

A further sub-class of compounds comprises those of the following formula (II):

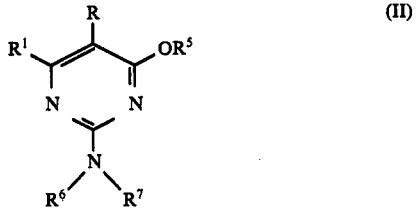

and acid addition salts thereof, wherein R, $R^1$, $R^5$, $R^6$ and $R^7$ can have any of the values previously assigned to them. Conveniently, $R^1$ is an alkyl group of 1 to 4 carbon atoms, for example a methyl group. The group R may be, for example, an alkyl or alkenyl radical of 3 to 4 carbon atoms. Alternatively the groups R and $R^1$ may jointly form a trimethylene or tetramethylene radical, which, with the pyrimidine ring atoms to which they are attached, will form a 5- or 6-membered ring. The group $R^5$ may be, for example, an alkyl or alkenyl radical of from 1 to 4 carbon atoms. Preferably, in the group —$NR^6R^7$ of formula (II), one of the groups $R^6$ and $R^7$ is a hydrogen atom and the remaining group is an alkyl or alkenyl radical of 1 to 3 carbon atoms.

A further sub-class of compounds for use in the process of the invention comprise those of the following formula (III):

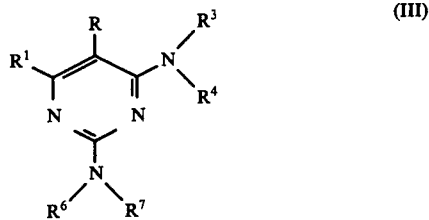

and acid addition salts thereof wherein R is an aliphatic or alicyclic group and $R^1$, $R^3$, $R^4$, $R^6$ and $R^7$ may have any of the values previously assigned to them. Conveniently, $R^1$ in formula (III) may be, for example, an alkyl group of 1 to 4 carbon atoms, for example a methyl group, and R may be, for example an alkyl or alkenyl group of 1 to 8 carbon atoms optionally substituted by phenyl, or R and $R^1$ may jointly form a trimethylene or tetramethylene radical. Preferably, in the group $-NR^3R^4$ both $R^3$ and $R^4$ are alkyl or alkenyl groups of 1 to 3 carbon atoms, or $R^3$ and $R^4$, together with the nitrogen atom to which they are attached, form a pyrrolidine, piperidine, or morpholine ring. Preferably, in the group $-NR^6R^7$, one of the groups $R^6$ and $R^7$ is a hydrogen atom and the remaining group is an alkyl or alkenyl radical of from 1 to 3 carbon atoms.

Particular examples of compounds for use in the process of the invention are listed in Table I below, together with a characterising physical constant.

TABLE I

| COMPOUND NO | $R^1$ | R | X | $-NR^6R^7$ | MELTING POINT °C |
|---|---|---|---|---|---|
| 1 | $CH_3$ | H | $OC_2H_5$ | $NHC_2H_5$ | 40–41 |
| 2 | $CH_3$ | H | $OCH_2CH(CH_3)_2$ | $NHC_2H_5$ | 42–43 |
| 3 | $CH_3$ | H | $OC_4H_9$ | $NHCH_3$ | 63–64 |
| 4 | $CH_3$ | H | $OC_4H_9$ | $NHC_2H_5$ | 35–37 |
| 5 | $CH_3$ | H | $OC_4H_9$ | $NHCH_2CH=CH_2$ | 49–51 |
| 6 | $CH_3$ | H | $OC_4H_9$ | $NHCH_2CHC_4H_9$ <br> $\vert$ <br> $C_2H_5$ | Oil <br> $n_D^{26}$ 1.4878 |
| 7 | $CH_3$ | H | $OC_4H_9$ | $NHCHCH_2CH(CH_3)_2$ <br> $\vert$ <br> $CH_3$ | Oil |
| 8 | $CH_3$ | H | $OC_5H_{11}$ | $NHC_2H_5$ | 48–48 |
| 9 | $CH_3$ | $CH_2C_6H_5$ | $OC_2H_5$ | $NHC_2H_5$ | 60–62 |
| 10 | $CH_3$ | $CH(CH_3)_2$ | $OC_3H_7$ | $NHC_2H_5$ | 47–48 |
| 11 | $CH_3$ | $C_3H_7$ | $OCH_3$ | $NHC_2H_5$ | 58.5–60.5 |
| 12 | $CH_3$ | $C_3H_7$ | $OC_2H_5$ | $NHCH_3$ | 56.5–59 |
| 13 | $CH_3$ | $C_3H_7$ | $OCH(CH_3)_2$ | $NHCH_2CH=CH_2$ | 70–72 |
| 14 | $CH_3$ | $CH_2CH(CH_3)_2$ | $OCH_3$ | $NHCH_2-CH=CH_2$ | 44.5–45.5 |
| 15 | $CH_3$ | $CH_2CH(CH_3)_2$ | $OCH(CH_3)_2$ | $NHC_2H_5$ | 78–80 |
| 16 | $CH_3$ | $CH_2CH(CH_3)_2$ | $OC_2H_5$ | $NHCH(CH_3)_2$ | Oil |
| 17 | $CH_3$ | $CH_2CH(CH_3)_2$ | $OC_3H_7$ | $NHCH_3$ | 66–68 |
| 18 | $CH_3$ | $C_4H_9$ | $OCH_3$ | $NHC_2H_5$ | 52–53 |
| 19 | $CH_3$ | $C_4H_9$ | $OCH_3$ | $NHCH(CH_3)_2$ | Oil |
| 20 | $CH_3$ | $C_4H_9$ | $OC_2H_5$ | $NHC_2H_5$ | 38–39 |
| 21 | $CH_3$ | $C_4H_9$ | $OCH_2CH=CH_2$ | $NHC_2H_5$ | Oil |
| 22 | $CH_3$ | $C_4H_9$ | $OCH(CH_3)_2$ | $NHCH_3$ | 60–63 |
| 23 | $CH_3$ | $C_4H_9$ | $OCH(CH_3)_2$ | $N(CH_3)_2$ | Oil |
| 24 | $CH_3$ | $C_4H_9$ | $OCH(CH_3)_2$ | $NHC_2H_5$ | 63–64 |
| 25 | $CH_3$ | $C_4H_9$ | $OCH_2CH=CH_2$ | $NHCH=CH_2$ | 41–43 |
| 26 | $CH_3$ | $C_4H_9$ | $OC_3H_7$ | $NHC_2H_5$ | 39.5–41.5 |
| 27 | $CH_3$ | $C_4H_9$ | $OC_3H_7$ | $NHCH_2CH=CH_2$ | 55–56 |
| 28 | $CH_3$ | $C_4H_9$ | $OCH_2CH(CH_3)_2$ | $NHCH_3$ | 47–50 |
| 29 | $CH_3$ | $C_4H_9$ | $OCH_2CH(CH_3)_2$ | $NHC_2H_5$ | 31–33 |
| 30 | $CH_3$ | $C_4H_9$ | $OCH_2CH=CHCH_3$ | $NHC_2H_5$ | Oil <br> $N_D^{25}$ 1.5138 |
| 31 | $CH_3$ | $C_4H_9$ | $OC_4H_9$ | $NHC_2H_5$ | 33.5–33.5 |
| 32 | $CH_3$ | $C_4H_9$ | $OC_4H_9$ | $NHCH(CH_3)_2$ | Oil |
| 33 | $CH_3$ | $C_4H_9$ | $OCH_2CH(CH_3)_2$ | $NHC_2H_5$ | Oil |
| 34 | $CH_3$ | $C_4H_9$ |  | $NHC_2H_5$ | 69–72 |
| 35 | $CH_3$ | $C_4H_9$ | O—⟨cyclohexyl⟩—O—⟨cyclohexyl⟩ | $N(CH_2)_2$ | Oil |
| 36 | $CH_3$ | $C_4H_9$ | $NHCH_2CH(CH_3)_2$ | $NHC_2H_5$ | 56.5–58.5 |
| 37 | $CH_3$ | $C_4H_9$ | $NHC_6H_{13}$ | $N(CH_3)_2$ | Oil |
| 38 | $CH_3$ | $CH_2CH(CH_3)_2$ | $NHC_3H_7$ | $NHCH_3$ | 83–85 |
| 39 | $CH_3$ | $C_4H_9$ | $NHC_8H_{17}$ | $N(CH_3)_2$ | Oil |
| 40 | $CH_3$ | $C_4H_9$ | $NHCH_2CH(CH_3)_2$ | $NHC_2H_5$ | 40–44 |
| 41 | $CH_3$ | $CH_2C_6H_5$ | $-N(CH_3)_2$ | $NHC_2H_5$ | 99–101 |

TABLE I-continued $$\begin{array}{c} R \\ R^1 \diagdown \diagup X \\ \diagdown N \quad N \diagup \\ NR^6R^7 \end{array}$$

| COMPOUND NO | R¹ | R | X | —NR⁶R⁷ | MELTING POINT °C |
|---|---|---|---|---|---|
| 42 | CH₃ | CH(CH₃)₂ | —N(piperidino) | NHC₂H₅ | 185–187 |
| 43 | CH₂CH(CH₃)₂ | CH(CH₃)₂ | N(piperidino) | NHC₂H₅ | Oil |
| 44 | CH₃ | C₃H₇ | N(C₂H₅)₂ | NHCH₃ | 46–49 |
| 45 | CH₃ | C₄H₉ | N(CH₃)₂ | NHC₂H₅ | 49–50 |
| 46 | CH₃ | C₄H₉ | N(CH₃)₂ | NHCH(CH₃)₂ | 31–34 |
| 47 | CH₃ | C₄H₉ | N(C₂H₅)₂ | NHC₂H₅ | 28–30 |
| 48 | CH₃ | C₄H₉ | N(pyrrolidino) | NHC₂H₅ | 80–81 |
| 49 | CH₃ | C₄H₉ | N(morpholino) | NHC₂H₅ | 49–50 |
| 50 | CH₃ | C₄H₉ | N(piperidino) | NHC₂H₅ | 44–47 |
| 51 | CH₃ | C₄H₉ | N(piperidino) | NHCH(CH₃)₂ | 38–40 |
| 52 | CH₃ | C₄H₉ | N(piperidino) | NHCH₂CH=CH₂ | 41–43 |
| 53 | CH₃ | C₇H₁₅ | N(piperidino) | NHC₂H₅ | 41–42.5 |
| 54 | CH₃ | CH₂CH=CH₂ | OCH₂CH=CH₂ | NHC₂H₅ | 40–41 |
| 55 | CH₃ | CH₃ | N(piperidino) | NHCH₃ | 99.5–100.5 |

Physical constants for liquid compounds of Table I

| COMPOUND NO | PHYSICAL CONSTANT |
|---|---|
| 7 | $n_D^{20}$ 1.4954 |
| 16 | $n_D^{20}$ 1.5023 |
| 19 | $n_D^{20}$ 1.5095 |
| 21 | $n_D^{27}$ 1.5152 |
| 23 | $n_D^{20}$ 1.4984 |
| 32 | $n_D^{18}$ 1.4995 |
| 33 | $n_D^{20}$ 1.5052 |
| 35 | Boiling point 110–118°/0.07 mm Hg |
| 37 | $n_D^{20}$ 1.5173 |
| 39 | $n_D^{20}$ 1.4989 |
| 43 | $n_D^{18}$ 1.5308 |

Broadly speaking the compounds of the invention are more effective to severely damage or kill unwanted plants when they are applied directly to the plants ("post-emergence application") that when they are applied to soil to prevent the emergence of seedlings of the unwanted plants ("pre-emergence application"). However, compounds of the subclass represented by formula (I) above are significantly effective by pre-emergence application as well as by post-emergence application. The rate of application required to severely damage or kill unwanted plants will depend upon the identity of the plants and upon the particular compound chosen for use. The determination of appropriate rates of application for a herbicide is a routine matter for those skilled in the art, but by way of general guidance, a rate of from 1 to 10 kilograms per hectare is generally suitable while from 2 to 6 kilograms per hectare may be preferred.

When applied directly to plants (i.e. post-emergence application) the compounds used in the process of the invention are relatively less phytotoxic towards cereals (for example rice) and legumes than they are towards other species of plants. Accordingly, the compounds may be used as selective herbicides for weeds growing in legume and cereal crops. In another aspect, therefore, the invention provides a process of severely damaging or killing weeds in cereal or legume crops, which comprises applying a compound of the formula:

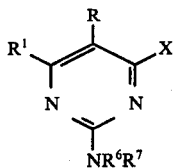

or an acid addition salt thereof, wherein R, $R^1$, X and $-NR^6R^7$ have any of the meanings previously assigned to them, to the area of the growing crop in an amount sufficient to severely damage or kill the weeds, but insufficient to damage the crop substantially. The rate at which the compound is to be applied will depend upon the particular compound chosen for use, but by way of general guidance, a rate of from 2 to 6 kilograms per hectare is usually suitable.

Compounds of the subclass represented by the formula (I) above are, as previously noted, herbicidally active when applied as a pre-emergence treatment as well as by post-emergence application. Accordingly, in addition to their use as selective post-emergence herbicides for cereal and legume crops, such compounds may also be used as pre-emergence selective herbicides for these crops. It has also been found that cotton is relatively more tolerant of pre-emergence application of compounds of the subclass represented by formula (I) than of post-emergence application. Accordingly, in a further aspect, the invention provides a process of inhibiting the growth of weeds in crops of cotton, cereals, and legumes, which comprises applying to the crop area, before the crop emerges, a compound of formula (I), in an amount sufficient to inhibit the growth of weeds, but insufficient to damage the crop substantially. The rate at which the compounds are to be applied may vary, depending for example on the identity of the crop, but will usually be in the range from 2 to 6 kilograms per hectare.

The compounds used in the process of the invention are preferably applied in the form of a composition, in which the active ingredient is mixed with a diluent or carrier. In another aspect therefore, the invention provides a herbicidal composition, comprising as an active ingredient a pyrimidine compound of the formula:

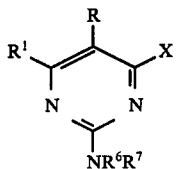

or an acid addition salt thereof, wherein R, $R^1$, X and $-NR^6R^7$ have any of the meanings previously assigned to them, in admixture with a solid or liquid diluent. Preferably the composition further comprises a surface-active agent.

The solid compositions of the invention may be, for example, in the form of dusting powders, or may take the form of granules. Suitable solid diluents include, for example, kaolin, bentonite, kieselguhr, dolomite, calcium, carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. One form of liquid composition according to the invention comprises an aqueous solution of an acid addition salt of a pyrimidine compound as hereinbefore defined. A preferred acid addition salt is the hydrochloride. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic monoesters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisoproyl-naphthalenesulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient. The concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment. In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10.0% and preferably between 0.1% and 1% by weight of the active ingredient.

In another aspect, the invention provides herbicidal pyrimidine compounds of the formula:-

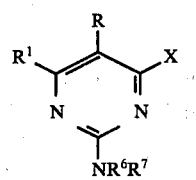

and acid addition salts thereof, wherein $R^1$, R, X and $NR^6R^7$ have any of the values previously assigned to them.

The compounds provided by the invention may be prepared in a variety of ways, as illustrated in Scheme A below:-

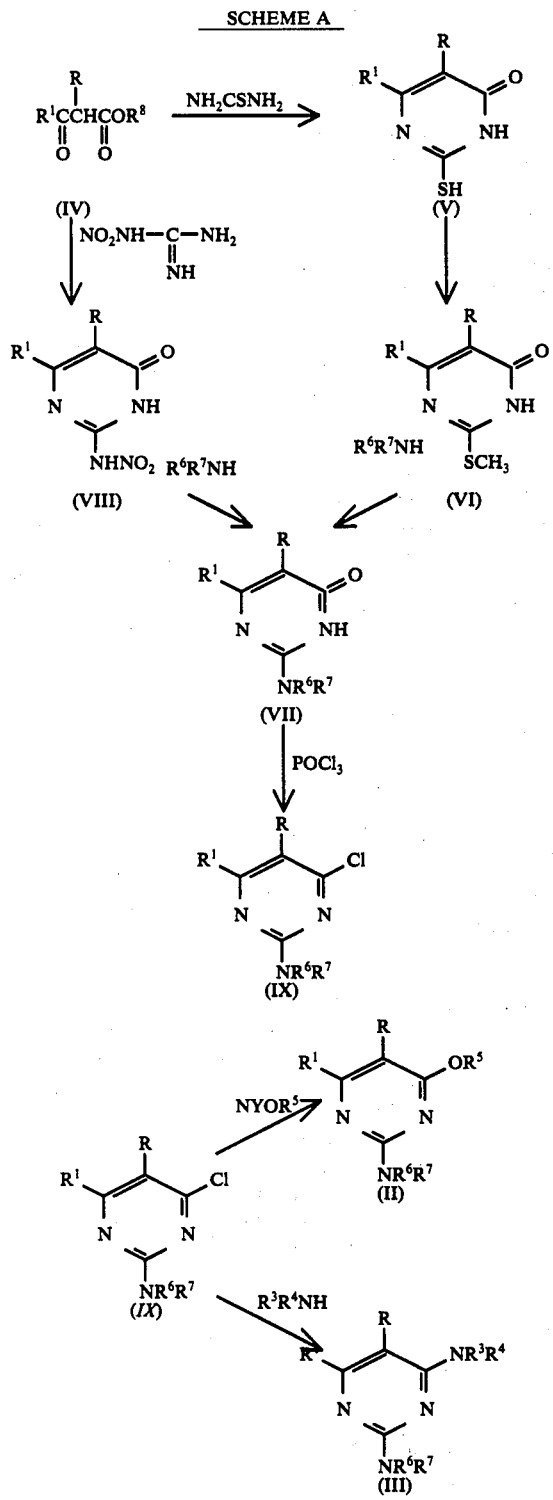

In Scheme A, the symbols R, $R^1$, $R^3$, $R^4$, $R^5$, $R^6$ and $R^7$ have any of the meanings previously assigned to them. The symbol $R^8$ represents a lower hydrocarbyl radical, for example in aliphatic radical. Conveniently $R^8$ is an alkyl radical of 1 to 6 carbon atoms. The symbol $MOR^5$ represents a metal derivative of an alcohol $R^5OH$. The metal may conveniently be an alkali metal, for example sodium or potassium.

According to scheme A, compounds according to the invention may be prepared by starting with an acyl acetic ester derivative (IV) and reacting this with thiourea to obtain a 2-mercaptopyrimidinone derivative (V). This mercapto pyrimidinone is then converted to a 2-methylthio-pyrimidine (VI) by treatment with a suitable methylating agent, for example dimethyl sulphate or methyl iodide, in the presence of a base, for example aqueous or ethanolic sodium hydroxide. The 2-methylthio derivative (VI) is then converted to the corresponding 2-aminopyrimidine derivative (VII) by reaction with the appropriate amine $R^6R^7NH$. The conversion may be carried out by heating the amine with the 2-methylthio derivative. Conveniently the amine is used in the reaction in the form of its salt with a lower alkanoic acid, for example acetic acid, as illustrated in Example 4. The temperature for carrying out the reaction may be readily established by experiment but by way of general guidance from 100° to 150° C is usually suitable.

The 2-aminopyrimidine derivative may also be prepared by an alternative route shown on the left hand side of Scheme A. According to this method, an acylacetic ester derivative (IV) is condensed with nitroguanidine to give the 2-nitroamino pyrimidine (VIII) as illustrated in Example 1. The 2-nitramino compound (VIII) so obtained is then heated with an amine $R^6R^7NH$ to obtain the 2-aminopyrimidine derivative (VII). Conveniently the amine $R^6R^7NH$ is used in the form of its salt with a lower alkanoic acid, for example the acetate salt with a lower alkanoic acid, as illustrated in Example 3. The temperature appropriate to bring about reaction is readily determined by simple experiment but by way of general guidance a temperature of 100° to 150° C is usually suitable.

Alternative methods of preparing the 2-aminopyrimidinone derivative represented by formula (VII) will be evident to those skilled in the art.

The 2-aminopyrimidine derivative (VII) is next converted into the 4-chloropyrimidine derivative (IX) by heating with phosphorus oxychloride as illustrated in Example 5.

The 4-chloropyrimidine so obtained may then be reacted either with a metal derivative of an alcohol $MOR^5$ to give the 4-$OR^5$ substituted derivatives (II) provided by the invention as illustrated in Example 6, or with an amine $R^3R^4NH$ to give the 2,4-diamino derivatives (III), as illustrated in Example 7.

Acid addition salts of the compounds used in the process of the invention may be prepared by conventional methods well known to those skilled in the chemical art. The compound may, for example, be dissolved in an aqueous solution containing an appropriate amount of the selected acid and the acid addition salt so formed may if desired be isolated by conventional methods, for example by evaporation of the solution or by precipitation of the salt by addition of water-miscible organic solvents.

The invention is illustrated by the following Examples in which all parts are by weight and all temperatures in degrees Centrigrade unless otherwise stated.

EXAMPLE 1

This Example illustrates the preparation of 2-nitramino pyrimidines of the formula (VIII) in Scheme A.

Nitroguanidine (53.1 g) was added to a solution of sodium (17.6 g) in methanol (500 ml). The mixture was heated under reflux for 45 minutes. Ethyl α-isobutylacetoacetate (95.0 g) was then added dropwise to the refluxing mixture over 30 minutes. Refluxing was continued for a further 6½ hours. Most of the methanol was removed and the residue was dissolved in water. Unreacted β-keto-ester was removed by extraction with chloroform and the solution was acidified with concentrated hydrochloric acid. The separated solid was washed with water and dried, giving 5-isobutyl-6-methyl-2-nitraminopyrimid-4(3H)-one (formula IV, $R^1$ = $CH_3$, R = isobutyl) (73.2 g). A sample recrystallised from ethanol had a melting point of 179°–181° (decomp.).

The following compounds of formula (IV) were similarly prepared:-

| $R^1$ | R | MELTING POINT °C |
|---|---|---|
| $CH_3$ | iso $C_3H_7$ | 181.5–182.5 |
| $CH_3$ | iso $C_4H_9$ | 179–181 |
| $CH_3$ | $C_3H_7$ | 199 |
| $CH_3$ | $C_4H_9$ | 160–161 (dec) |
| —$CH_2CH_2CH_2CH_2$— | | 215–218 |
| $CH_3$ | H | 243 (dec) |

EXAMPLE 2

This Example illustrates the preparation of 2-methylmercapto pyrimidines of formula (VI) in Scheme A above.

(a) Preparation of 4-methyl-5-propyl-2-thiopyrimidine-6(1H)-one (formula (V), $R^1$ = $CH_3$, R = $C_3H_7$).

This compound was prepared according to the procedure described by Chi, J. Amer. Chem. Soc., 1936, 58, 1150 for the preparation of the corresponding 5-butyl compound, by heating ethyl α-propylacetoacetate, thiourea, and sodium ethoxide under reflux in ethanol for 10 hours. The excess of alcohol was removed, the residue taken up in water, and acidified with acetic acid, and the precipitated thiopyrimidine collected; it had a melting point of 210°–212° C.

(b) Preparation of 4-methyl-2-methylthio-5-propylpyrimidine-6(1H)-one (formula (VI, $R^1$ = $CH_3$, R = $C_3H_7$).

Dimethylsulphate (50.4 g) was added slowly to a solution of 4-methyl-5-propyl-2-thiopyrimidin-6(1H)-one (69.0 g) in water (500 ml) containing sodium hydroxide (20.0 g). The mixture was vigorously stirred at room temperature for 3 hours and the precipitated methylthio compound collected (40 g). A sample recrystallised from toluene had a melting point of 184.5°–185.5° C.

The following compounds of formula (VI) were similarly prepared:-

| $R^1$ | R | MELTING POINT °C |
|---|---|---|
| $CH_3$ | $C_3H_7$ | 184.5–185.5 |
| $CH_3$ | $C_4H_9$ | 159 |
| $CH_3$ | $CH_2Ph$ | 218–219 |
| $CH_3$ | H | 214–218 |

EXAMPLE 3

This Example illustrates the preparation of a compound of formula VII of scheme A from a compound of formula (VIII).

5-Isobutyl-6-methyl-2-nitraminopyrimid-4(3H)-one (16.0 g) was mixed with ethylamine acetate (30 g) and heated without solvent at 120° C for 6 hours. The melt was cooled and water was added. The mixture was brought to pH 5 and the precipitated product recrystalised from aqueous acetone to give 2-ethylamino-5-isobutyl-6-methylpyrimid-4(3H)-one (formula VII, $R^1$ = $CH_3$, R = is $C_4H_9$, $R^6$ = H, $R^7$ = $C_2H_5$) having a melting point of 203°–204° C.

EXAMPLE 4

This Example illustrates the preparation of a compound of formula VII from a 2-methylthio compound of formula (VI).

A mixture of allylamine acetate (12 g) and 6-methyl-2-methylthio-5-propylpyrimid-4(3H)-one (6 g) was heated at 130° C for 45 minutes. The mixture was cooled and water was added. The precipitated product was collected, washed with water, dried and recrystalised from petroleum (b.p. 80°–100° C) giving 2-allylamino-6-methyl-5-propylpyrimid-4(3H)-one (formula VII, $R^1$ = $CH_3$, R = $C_3H_7$, $R^6$ = H, $R^7$ = $CH_2CH=CH_2$) having a melting point of 152°–153° C.

EXAMPLE 5

This Example illustrates the conversion of the pyrimidone compounds (VII) to the 4-chloropyrimidines (IX). (1X).

The conversion is illustrated by the preparation of 5-butyl-4-chloro-2-ethylamino-6-methylpyrimidine (formula 1X, $R^1$ = $CH_3$, R = $C_4H_9$, $R^6$ = $NHC_2H_5$, $R^7$ = H). 5-Butyl-2-ethyl-amino-4-methyl pyrimidine-6(1H)-one (209 g) and phosphorus oxychloride (460 ml) were heated under reflux for 3 hours. The excess of phosphorus oxychloride was distilled off under reduced pressure and the residue poured on to crushed ice. The mixture was neutralised with aqueous ammonia solution and the white solid collected. The solid was dissolved in chloroform and the solution dried and evaporated to give an oil. Trituration with warm petroleum (b.p. 40°–60° C) and cooling gave the chloro compound (151.0 g) having a melting point of 76°–77° C.

The following compounds of formula IX were similarly prepared:-

| $R^1$ | R | $R^6R^7N$— | MELTING POINT °C |
|---|---|---|---|
| $CH_3$ | iso $C_3H_7$ | $NHCH_2CH=CH_2$ | 39–40.5 |
| $CH_3$ | iso $C_3H_7$ | $NHC_2H_5$ | 50–51 |
| $CH_3$ | $C_3H_7$ | $NHC_2H_5$ | 65.5–66.5 |
| $CH_3$ | $C_3H_7$ | $NHCH_3$ | 123.5–124.5 |
| $CH_3$ | $C_3H_7$ | $NHCH_2$—$CH=CH_2$ | 58.5–61.5 |
| $CH_3$ | $C_4H_9$ | $NHCH_2CH=CH_2$ | 63–65 |
| $CH_3$ | $C_4H_9$ | $NHC_2H_5$ | 78–79 |
| $CH_3$ | $C_4H_9$ | $NHCH_3$ | 94–96 |
| $CH_3$ | $C_4H_9$ | $NHCH(CH_3)_2$ | 46–48 |
| $CH_3$ | $C_4H_9$ | $NHC_3H_7$ | |

-continued

| R$^1$ | R | R$^6$R$^7$N— | MELTING POINT ° C |
|---|---|---|---|
| CH$_3$ | CH$_2$CH(CH$_3$)$_2$ | NHCH$_3$ | 89–90 |
| CH$_3$ | CH$_2$CH(CH$_3$)$_2$ | NHC$_2$H$_5$ | 79–81 |
| CH$_3$ | CH$_2$CH(CH$_3$)$_2$ | NHCH(CH$_3$)$_2$ | 65–75 |
| CH$_3$ | CH$_2$CH(CH$_3$)$_2$ | NHCH$_2$CH=CH$_2$ | 74–76 |
| CH$_3$ | CH$_2$C$_6$H$_5$ | NHC$_2$H$_5$ | 113–115 |
| CH$_3$ | C$_7$H$_{15}$ | NHC$_2$H$_5$ | 58–61 |
| CH$_3$ | C$_4$H$_9$ | N(CH$_3$)$_2$ | B.p. 99–106/0.2 mm |
| CH$_2$CH(CH$_3$)$_2$ | CH(CH$_3$)$_2$ | NHC$_2$H$_5$ | 53–56 |
| CH$_3$ | H | NHCH$_2$CH=CH$_2$ | 75–76 |
| CH$_3$ | H | NHCH$_3$ | 136–137 |
| CH$_3$ | H | NHC$_2$H$_5$ | 93–93.5 |
| CH$_3$ | H | NHCHCH$_2$CHCH$_3$<br>   \|          \|<br>   CH$_3$   CH$_3$ | $n_D^{20}$ 1.5252 |
| CH$_3$ | H | NHCH$_2$CHC$_4$H$_9$<br>   \|<br>   C$_2$H$_5$ | $n_D^{18}$ 1.5192 |

EXAMPLE 6

This Example illustrates the preparation of compounds of formula (II) of Scheme A, by reference to the preparation of 5-butyl-2-ethylamino-4-methyl-6-propoxypyrimidine (compound no. 26 of Table I). 5-Butyl-4-chloro-2-ethylamino-6-methylpyrimidine (2.28 g) was added to a solution of sodium (0.46 g) in n-propanol (50 ml). The mixture was heated under reflux for 20 hours and poured into water. The product was extracted with chloroform and the extracts dried and evaporated to give an oil which solidified on standing. The solid was recrystallised from methanol-water to give the propoxy compound (2.45 g) having a melting point of 39.5°–41.5° C. Compounds 1 to 25, 27 to 35 and 54 of Table I were analogously prepared.

EXAMPLE 7

This Example illustrates the preparation of compounds of formula (III) of Scheme A, by reference to the preparation of 5-butyl-2-ethylamino-4-methyl-6-pyrrolidinylpyrimidine (Compound No. 48 of Table I). Pyrrolidine (3.55g) was added to a solution of 5-butyl-4-chloro-2-ethylamino-6-methyl-pyrimidine (2.28g) in glacial acetic acid (2.0g) and the mixture heated at 155°–165° C for 2 hours. The mixture was cooled and water was added. The mixture was made alkaline with sodium hydroxide and the product collected and recrystallised from ethanol-water, yielding the pyrrolidinyl compound (2.07g) (compound No.48 of Table I) having a melting point of 80°–81° C. Compounds 36 to 47, 49 to 53 and 55 of Table I were similarly prepared.

EXAMPLE 8

This Example illustrates the herbicidal properties of compounds used in the process of the invention. Each compound (0.12g) was formulated for test by mixing it with 5 ml of an emulsion prepared by diluting 100 ml of a solution containing 21.8 grams per liter of Span 80 and 78.2 grams per liter of Tween 20 in methyl cyclohexanone to 500 ml with water. Span 80 is a Trade Mark for a surface active agent comprising sorbitan monolaurate. Tween 20 is a Trade Mark for a surface-active agent comprising a condensate of twenty molar proportions of ethylene oxide with sorbitan mono-oleate. The mixture of the compound and the emulsion was shaken with glass beads and diluted to 12 ml with water.

The srpay composition so prepared was sprayed on to young pot plants (post-emergence test) of the species named in Table II below, at a rate equivalent to 1000 liters per hectare (10 kilograms of pyrimidine compound per hectare). Damage to plants was assessed 14 days after spraying by comparison with untreated plants, on a scale of 0 to 3 where 0 is no effect and 3 represents 75 to 100% kill. In a test for pre-emergence herbicidal activity, seeds of the test species were placed on the surface of fibre trays of soil and were sprayed with the compositions at the rate of 1000 liters per hectare. The seeds were then covered with further soil. Fourteen days after spraying, the seedlings in the sprayed fibre trays were compared with the seedlings in unsprayed control trays, the damage being assessed on the same scale of 0 to 3. The results are given in Table II below:-

TABLE II

| COMPOUND NO | PRE- OR POST-EMERGENCE APPLICATION | TEST PLANTS | | | | | |
|---|---|---|---|---|---|---|---|
| | | Le | To | Cl | Wh | Dg | Pr |
| 1 | Pre | 2 | 1 | 1 | 0 | 0 | 0 |
|   | Post | 0 | 1 | 1 | 0 | 1 | 0 |
| 16 | Post | 3 | 3 | 3 | 2 | 2 | 1 |
| 23 | Post | 1 | 0 | 1 | 0 | 2 | 0 |
| 24 | Post | 3 | 3 | 3 | 1 | 3 | 0 |
| 28 | Post | 0 | 2 | 2 | 0 | 3 | 0 |
| 29 | Post | 3 | 3 | 3 | 1 | 3 | 1 |
| 34 | Post | 2 | 2 | — | 0 | 2 | 0 |
| 35 | Post | 2 | 3 | 3 | 2 | 3 | 2 |
| 36 | Post | 1 | 3 | 1 | 1 | 2 | 0 |
| 37 | Post | 0 | 3 | 1 | 0 | 1 | 0 |
| 38 | Post | 0 | 3 | 2 | 0 | 2 | 0 |
| 39 | Post | 2 | 3 | 1 | 1 | 3 | 0 |
| 40 | Post | 0 | 2 | 0 | 0 | 1 | 0 | the names of the test plants are as follows:-
Le — Lettuce
To — Tomato
Cl — Red Clover
Wh — Wheat
Dg — *Digitaria sanguinalis*
Pr — Perennial ryegrass (*Lolium perennum*)

Some compounds were tested on a different range of test plants. The test was carried out in just the same way except that the pre-emergence effect was assessed after 3 weeks, not two. The results are given in Table III below:- are) and a difference range of test plants. The results are given in Tables IV and V below, and are on a scale of 0 to 5 where 0 is no effect and 5 is complete kill. In the results, a dash(—) means that no test was made. In Table IV both pre- and post-emergence assessments were made at 2 weeks after applications. In Table V, assessments were at 3 weeks from the pre-emergence test and 2 weeks from the post-emergence test.

TABLE III

| COMPOUND NO | PRE- OR POST-EMERGENCE APPLICATION | TEST PLANTS |||||| 
|---|---|---|---|---|---|---|---|
| | | Le | To | Wo/O | Dg | Pr | Cp |
| 3 | Post | 1 | 2 | 2 | 0 | 0 | 0 |
| 6 | Pre | 2 | 0 | 0 | 3 | 0 | 0 |
| | Post | 2 | 3 | 1 | 1 | 1 | 0 |
| 8 | Pre | 1 | 2 | 1 | 2 | 2 | 0 |
| | Post | 3 | 2 | 3 | 2 | 0 | 0 |
| 30 | Post | 1 | 3 | 2 | 1 | 1 | 0 |
| 55 | Post | 3 | 3 | 0 | 0 | 0 | 0 |

The names of the test plants not common to Table II are as follows:-
Wo/O — Wild Oats (*Avenua fatua*) and cultivated oats (Wild oats are used in the post-emergence test and cultivated oats in the pre-emergence test).
Cp — *Cyperus rotundus*.

EXAMPLE 9

This Example further illustrates the herbicidal properties of compounds used in the process of the invention. Tests were carried out as described in Example 8, but using a lower application rate (5 kilograms per hectare)

TABLE IV

| COMPOUND NO | PRE- or POST-EMERGENCE APPLICATION | TEST PLANTS |||||||||||||||| 
|---|---|---|---|---|---|---|---|---|---|---|---|---|---|---|---|---|---|
| | | Sb | Rp | Ct | P | Sn | Ip | Am | Pa | Ca | Po | Mz | Br | Rc | Ot | Dg | El | Pn |
| 4 | Pre | 2 | 4 | 1 | 0 | 5 | 3 | 0 | 2 | 2 | 0 | 1 | — | 0 | 2 | 5 | 5 | 5 |
| | Post | 1 | 5 | 3 | 0 | 0 | 5 | 5 | 0 | 5 | 5 | 1 | — | 0 | 0 | 5 | 5 | 2 |
| 7 | Pre | 0 | 1 | 0 | 0 | 0 | 1 | — | — | 1 | 1 | 1 | 0 | — | 1 | 5 | 5 | 5 |
| | Post | 3 | 5 | 4 | 4 | 4 | 4 | 4 | 3 | 5 | 4 | 4 | 4 | 0 | 1 | 5 | 4 | 4 |
| 9 | Post | 4 | 5 | 4 | 1 | 5 | 5 | 5 | 5 | 5 | 5 | 0 | 2 | 0 | 0 | 5 | 5 | 5 |
| 10 | Post | 5 | 5 | 5 | 2 | 5 | 5 | 5 | 5 | 5 | 5 | 4 | 4 | 0 | 3 | 4 | 5 | 3 |
| 11 | Post | 2 | 5 | 1 | 3 | 5 | 5 | 5 | 0 | 4 | 4 | 1 | 2 | 0 | 1 | 4 | 4 | 4 |
| 12 | Post | 5 | 5 | 0 | 3 | 5 | 5 | 5 | 1 | 5 | 4 | 1 | 2 | 0 | 2 | 1 | 5 | 2 |
| 13 | Post | 1 | 5 | 0 | 1 | 0 | 5 | 4 | 2 | 5 | 5 | 0 | 1 | 0 | 0 | 0 | 5 | 3 |
| 14 | Post | 2 | 5 | 4 | 0 | 1 | 3 | 4 | 0 | 4 | 4 | 4 | 2 | 0 | 0 | 2 | 2 | 0 |
| 15 | Post | 3 | 5 | 4 | 1 | 0 | 5 | 0 | 0 | 4 | 5 | 3 | 2 | 0 | 1 | 3 | 5 | 3 |
| 17 | Post | 0 | 5 | 4 | 1 | 3 | 5 | 5 | 4 | 5 | 5 | 4 | 0 | 0 | 1 | 5 | 4 | 1 |
| 18 | Post | 3 | 4 | 4 | 3 | 5 | 5 | 5 | 3 | 5 | 5 | — | 2 | 0 | 2 | 5 | 4 | 3 |
| 19 | Post | 1 | 5 | 4 | 4 | 5 | 5 | 5 | 4 | 5 | 5 | 3 | 1 | 0 | 0 | 4 | 5 | 3 |
| 20 | Post | 4 | 5 | 4 | 4 | 5 | 5 | 5 | 3 | 5 | 5 | 1 | 1 | 0 | 0 | 5 | 4 | 4 |
| 21 | Post | 5 | 5 | 1 | 3 | 5 | 5 | 5 | 3 | 5 | 5 | 2 | 3 | 1 | 1 | 4 | 5 | 3 |
| 22 | Post | 5 | 5 | 3 | 1 | 5 | 5 | 5 | 2 | 5 | 5 | 1 | 3 | 0 | 1 | 4 | 5 | 5 |
| 25 | Post | 2 | 5 | 3 | 4 | 3 | 4 | 4 | 1 | 5 | 5 | 2 | 2 | 0 | 0 | 4 | 4 | 1 |
| 26 | Post | 2 | 5 | 2 | 0 | 3 | 4 | 5 | 1 | 5 | 4 | 1 | 1 | 0 | 0 | 4 | 2 | 3 |
| 27 | Post | 4 | 5 | 5 | 0 | 3 | 5 | 5 | 5 | 4 | 5 | 3 | 2 | 0 | 1 | 4 | 5 | 4 |
| 31 | Post | 3 | 5 | 4 | 1 | 5 | 5 | 5 | 3 | 5 | 5 | — | 1 | 0 | 2 | 5 | 4 | 4 |
| 32 | Post | 5 | 5 | 3 | 2 | 1 | 5 | 5 | 5 | 5 | 5 | 4 | 3 | 1 | 2 | 4 | 5 | 5 |
| 33 | Post | 2 | 5 | 4 | 3 | 2 | 4 | 4 | 4 | 4 | 5 | 4 | 3 | 2 | 1 | 4 | 4 | 4 |
| 42 | Post | 2 | 5 | 4 | 3 | 4 | 4 | 5 | 3 | 4 | 4 | 1 | 1 | 0 | 0 | 2 | 5 | 1 |
| 43 | Post | 2 | 5 | 4 | 2 | 5 | 5 | 5 | 3 | 5 | 4 | 3 | 3 | 0 | 2 | 4 | 5 | 3 |
| 44 | Post | 3 | 5 | 5 | 3 | 5 | 4 | 5 | 4 | 5 | 5 | 2 | 2 | 0 | 2 | 3 | 5 | 3 |
| 45 | Post | 5 | 5 | 0 | 2 | 5 | 5 | 5 | 2 | 4 | 5 | 3 | 2 | 0 | 1 | 4 | 5 | 4 |
| 46 | Post | 5 | 5 | 1 | 2 | 5 | 5 | 5 | 0 | 5 | 5 | 0 | 1 | 0 | 0 | 4 | 4 | 4 |
| 47 | Post | 5 | 5 | 4 | 4 | 5 | 4 | 5 | 4 | 5 | 5 | 4 | 1 | 0 | 0 | 3 | 4 | 3 |
| 48 | Post | 5 | 5 | 4 | 3 | 5 | 5 | 5 | 3 | 5 | 5 | 2 | 2 | 1 | 2 | 4 | 5 | 4 |
| 49 | Post | 2 | 5 | 0 | 1 | 5 | 5 | 5 | 2 | 5 | 5 | 2 | 3 | 0 | 1 | 5 | 4 | 2 |
| 50 | Post | 1 | 5 | 0 | 0 | 2 | 4 | 4 | 0 | 3 | 2 | 0 | 1 | 0 | 0 | 1 | 4 | — |
| 51 | Post | 5 | — | 5 | 2 | 5 | 5 | 5 | 5 | 5 | 5 | 4 | 3 | 1 | 1 | 5 | 5 | 5 |
| 52 | Post | 3 | 5 | 4 | 2 | 5 | 4 | 5 | 4 | 3 | 5 | 3 | 3 | 0 | 2 | 4 | 5 | 3 |
| 53 | Post | 5 | 5 | 5 | 4 | 5 | 5 | 5 | 1 | 5 | 5 | 0 | 1 | 0 | 1 | 3 | 5 | 4 |
| 54 | Post | 5 | 5 | 5 | 4 | 5 | 5 | 5 | 4 | 5 | 5 | 1 | 2 | 0 | 1 | 5 | 5 | 1 |

TABLE V

| COMPOUND NO | PRE- or POST-EMERGENCE APPLICATION | TEST PLANTS ||||||||||||||||||| 
|---|---|---|---|---|---|---|---|---|---|---|---|---|---|---|---|---|---|---|---|---|
| | | Sb | Rp | Ct | Sy | Mz | Wh | Rc | Sn | Ip | Am | Pa | Ca | Po | Ab | Cv | Ot | Dg | Pn | St | Ei | Sh | Ag | Cn |
| 2 | Pre | 5 | 5 | 1 | 5 | 4 | 4 | 4 | 5 | 5 | 5 | 4 | 5 | 4 | 4 | — | 5 | 5 | 5 | 5 | 5 | — | 1 | 0 |
| | Post | 2 | 0 | 0 | 4 | 0 | 0 | 1 | 0 | 3 | 2 | 0 | 1 | — | 1 | 2 | 0 | 1 | 1 | 0 | 0 | 0 | 0 | 0 |
| 5 | Pre | 3 | 5 | 0 | 1 | 2 | 3 | 3 | 4 | 0 | 4 | 0 | 5 | 3 | 0 | — | 4 | 5 | 5 | 3 | 3 | — | 0 | 0 |
| | Post | 2 | 1 | 1 | 3 | 0 | 0 | 0 | 0 | 0 | 2 | 0 | 3 | — | 1 | 1 | 0 | 0 | 2 | 0 | 0 | 0 | 0 | 0 |

The names of the test plants not already given in Example 8 are as follows:-

| Sb | Sugar beet | Sy | Soya bean |
|---|---|---|---|
| Rp | Rape | Ab | *Abutilon theophrastii* |
| Ct | Cotton | Cv | *Convolvulus arvensis* |
| P | Pea | Ot | Oats pre-emergence, |
| Sn | *Senecio vulgaris* | | *Avena fatua* post-emergence |
| Ip | *Ipomoea purpurea* | | |

| | | | |
|---|---|---|---|
| Am | Amaranthus retroflexus | St | Setaria viridis |
| Pa | Polygonum aviculare | Ec | Echinochloa crus-galli |
| Ca | Chenopodium album | Sh | Sorghum halepense |
| Portulaca oleracea | | | |
| Mz | Maize | Ag | Agropyron repens |
| Br | Barley | Cn | Cyperus rotundus in post-emergence test, Cyperus esculentus in pre-emergence test |
| Rc | Rice | | |
| Ot | Oats | | |
| El | Eleusine indica | | |
| Pn | Poa annua | | |

We claim:

1. A process of severely damaging or killing unwanted plants, which comprises applying to the plants, or to the growth medium thereof, a herbicidally effective amount of pyrimidine compound of the formula:-

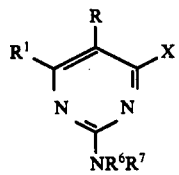

or a herbicidal acid addition salt thereof, wherein $R^1$ is an alkyl radical of 1 to 6 carbon atoms, cycloalkyl or alkenyl; R is a hydrogen atom or an alkyl or alkenyl radical of from 1 to 12 carbon atoms, which may be substituted by a phenyl radical; or $R^1$ and R taken together form a trimethylene or tetramethylene radical; X is a group $-OR^5$ wherein $R^5$ is an alkyl or alkenyl radical of 1 to 10 carbon atoms or cycloalkyl; and $R^6$ and $R^7$ each represent hydrogen or an alkyl or alkenyl radical of 1 to 8 carbon atoms, or cycloalkyl, or $R^6$ and $R^7$, taken together with the nitrogen atom to which they are attached constitute a pyrrolidinyl, piperidinyl, or morpholinyl ring.

2. A process according to claim 1, wherein the rate of application of the compound is from 1 to 10 kilograms per hectare.

3. A process of severely damaging or killing weeds in crops of cereals or legumes, which comprises applying a pyrimidine compound or a herbicidal acid addition salt thereof as defined in claim 1, to the area of the growing crop, in an amount sufficient to severely damage or kill the weeds, but insufficient to damage the crop substantially.

4. A process as claimed in claim 3 wherein the rate of application of the pyrimidine compound is from 2 to 6 kilograms per hectare.

5. A process of severely damaging or killing weeds in crops of cereals, legumes, or cotton, which comprises applying to the crop area, before the crop emerges, a pyrimidine compound of the formula:

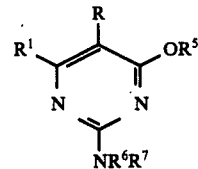

or a herbicidal acid addition salt thereof, wherein $R^1$, $R^5$, $R^6$ and $R^7$ are defined as in claim 1, in an amount sufficient to inhibit the growth of weeds but insufficient to damage the crop substantially.

6. A process according to claim 5 wherein the rate of application of the pyrimidine compound is from 2 to 6 kilograms per hectare.

* * * * *